United States Patent [19]

Bannon et al.

[11] Patent Number: 4,946,853

[45] Date of Patent: Aug. 7, 1990

[54] METHOD FOR THE TREATMENT OF WITHDRAWAL SYMPTOMS ASSOCIATED WITH SMOKING CESSATION AND PREPARATIONS FOR USE IN SAID METHOD

[75] Inventors: Yvonne B. Bannon, Naas; John Corish, Leopardstown; Owen I. Corrigan, Howth; Edward J. Geoghegan, Athlone; Joseph G. Masterson, Dublin, all of Ireland

[73] Assignee: Elan Transdermal Limited, Athlone, Ireland

[21] Appl. No.: 188,226

[22] Filed: Apr. 29, 1988

[30] Foreign Application Priority Data

May 1, 1987 [IE] Ireland .................................. 1119/87
Jul. 17, 1987 [IE] Ireland .................................. 1946/87

[51] Int. Cl.$^5$ ...................... A61K 31/44; A61K 31/78; A61F 13/02
[52] U.S. Cl. ........................................ 514/343; 424/81; 424/449; 424/485; 424/486; 514/813; 514/936; 514/944; 514/946
[58] Field of Search .................. 424/81, 195.1, 449, 424/486, 485; 514/936, 944, 946, 343, 813

[56] References Cited

U.S. PATENT DOCUMENTS 4,597,961 7/1986 Etscorn .................................. 424/28
4,675,009 6/1987 Hymes et al. ........................ 604/304
4,680,172 7/1987 Leeson ................................. 424/449

FOREIGN PATENT DOCUMENTS 0013606 7/1980 European Pat. Off. .
3438284 10/1984 Fed. Rep. of Germany .

OTHER PUBLICATIONS

Rose et al., Drug and Alcohol Dependence, 13, 209–213 (1984).

Rose et al., Clin. Pharmacol. Ther., vol. 38, No. 4 (Oct., 1985).

Primary Examiner—John W. Rollins
Attorney, Agent, or Firm—Marla J. Church

[57] ABSTRACT

A preparation for the once-daily, percutaneous administration of nicotine comprises nicotine uniformly distributed in a solid, semi-solid or mucilaginous medium which can be placed in intimate contact with the skin, the solid, semi-solid or mucilaginous medium is formed by adding a given amount of nicotine to a solution of a solidifying or gel-forming agent or mixture thereon in a suitable solvent or mixture of solvents and mixing or heating the mixture thereby obtained so as to form the solid, semi-solid or mucilaginous medium.

The preparation can be used in a method of treating withdrawal symptoms associated with smoking cessation and for combating the psychological dependence that occurs through frequency smoking.

43 Claims, No Drawings

METHOD FOR THE TREATMENT OF WITHDRAWAL SYMPTOMS ASSOCIATED WITH SMOKING CESSATION AND PREPARATIONS FOR USE IN SAID METHOD

BACKGROUND OF THE INVENTION

This invention relates to a method for the treatment of withdrawal symptoms associated with smoking cessation with preparations containing nicotine and such preparations.

Nicotine is the major alkaloid of tobacco and is the most potent alkaloid in tobacco smoke.

There is now strong evidence for regarding smoking as a form of drug dependence, the drug, of course, being nicotine. Measurements of the concentrations of nicotine, and its metabolite cotinine, in the blood of smokers have demonstrated the extent to which smoking is a drug taking activity. Rapid absorption through the lungs enables the smoker to get an intravenous-like shot of nicotine after each inhaled puff. By varying puff rate, puff volume and depth of inhalation, smokers regulate their nicotine intake and have literally finger-tip control over the concentrations of nicotine delivered to their brain. Nicotine has been shown to act as a primary reinforcer in animals and many of its pharmacological effects are potentially rewarding. It includes tolerances and smokers suffer from physical as well as subjective effects when it is withdrawn.

Nicotine induces changes in the number of nicotinic cholinergic receptors and this is one possible mechanism underlying tolerance. Besides its main direct action at nicotinic cholinergic receptor sites, through linkage of these sites with other neurotransmitter systems, nicotine has indirect effects on the release of most of the known neurotransmitters. Through its action on the locus coeruleus it has a widespread effect on noradrenergic activity throughout the brain. It also activates ascending dopaminergic pathways thought to be involved with the brainstem and hypothalamic reward systems. Its effect on dopaminergic activity may link in with the lower incidence of Parkinson's Disease among cigarette smokers. Nicotine also stimulates cholinergic neurones in the nucleus basalis of Meynert which in turn project to all regions of the cortex. This and similar actions on nerve cells in the septum, which project to the hippocampus, may be involved in the effect of nicotine on memory processes and suggest that nicotine may be of potential value in enhancing performance in people with early Alzheimer's Disease. Nicotine also influences serotonergic systems.

By smoking a cigarette, the smoker receives an initial burst of nicotine into the bloodstream, which then rapidly declines. The urge to smoke increases as the nicotine level continues to fall below a given point in the blood level, a point which can vary with each smoker. However, it has been shown that the normal plasma trough level associated with usual smoking is approximately 5–15 ng/ml within one hour of first smoking. At the time of smoking the plasma level is between 15 ng/ml and 30 ng/ml and the natural urge to smoke is thereby suppressed. When nicotine levels fall to a level of 15 ng/ml or less, nicotine intake is required to suppress the smoking urge. Thus the objective for any smoking cessation therapy involving nicotine administration would be the rapid attainment and maintenance of such plasma levels.

One of the approaches currently used in smoking cessation therapy using nicotine is that employed by a nicotine containing chewing gum sold under the Trade Mark NICORETTE. This gum contains a cation exchange resin containing 2 or 4 mg of nicotine. The release rate of nicotine from this gum is dependent upon the duration and vigour of chewing. There can be a considerable variation in absorption of nicotine from gum depending upon how a person chews the gum. To achieve adequate absorption of nicotine vigorous chewing is required. It has been reported that normal chewing results in over 90% of nicotine being released within 20 minutes. Thus the system requires frequent administration by the smoker in an attempt to maintain effective plasma levels and thus curb the urge to smoke. The plasma levels achieved by the 2 mg gum fail to achieve the levels measured after cigarette smoking and, therefore, the 4 mg gum would be required by the smoker in most cases.

Because buccal absorption is pH dependent, a buffer has been incorporated into the gum in an attempt to maintain the buccal environment at constant pH. While it is intended that this buffer maintain the pH in the mouth at approximately 8.5, there is no experimental data in the literature to support this conclusion. Such pH control is of considerable importance in relation to both the extent and variability of absorption of nicotine into the bloodstream from this site of administration.

Another feature of such oral nicotine administration is the susceptibility of the patient to gastrointestinal upsets. Also the poor taste qualities associated with oral nicotine administration makes such a method of smoking cessation unpopular with the patient and thus can lead to poor compliance, even to the level of resumption of cigarette smoking.

A major problem in maintaining continuous effective therapeutic levels of nicotine in the bloodstream with the nicotine gum is the inability to self-administer during the time the patient is asleep, thus leading to low or even zero levels of nicotine in the morning and a return of the smoking urge. Even with immediate administration of the nicotine gum, it can take up to one hour before effective plasma levels of nicotine are again attained.

Additionally, the mode of administration of the gum, in that it involves frequent dosage and chewing, is a practice which is widely regarded as being socially unacceptable. Generally, gum will have to be chewed at the same frequency as the person's smoking pattern and usually every hour to achieve adequate plasma levels of nicotine. With gum there is no assistance in breaking the smoking habit.

Another aspect of oral nicotine administration in the gum form, is that there is now a suggestion of the chance of contracting cancer of the mouth and throat, as a result of frequent chewing of resin based nicotine containing gum. Mouth ulcers have also been observed in persons chewing nicotine gum.

Another development has been the introduction of low-nicotine cigarettes. However, again with such low-nicotine cigarettes there is no breaking of the smoking habit.

In a study by Jed E. Rose et al reported in Clin. Pharmacol. Ther. October 1985 a 30% aqueous solution of nicotine base was applied to intact skin under an opaque polyethylene patch. The purpose of the patch was to prevent subjects observing any changes in skin colour such as redness. With such a solution immediate release of nicotine was observed. However, painting on of a nicotine solution as described by Jed E. Rose et al would not be socially acceptable.

Nicotine is known to show a high degree of absorption by the percutaneous route. A method for the percutaneous or transdermal administration of nicotine is known from U.S. Pat. No. 4,597,961. However, nicotine has not heretofore been used commercially by the percutaneous or transdermal route in a method of smoking cessation therapy. Various devices for the percutaneous or transdermal administration of nicotine are disclosed in U.S. Pat. No. 4,597,961. However, these are clearly not commercial devices. U.S. Pat. No. 4,597,961 refers to a dose range of nicotine of 15 to 25 ng/l or 15 to 25 picograms/ml. However, as indicated above trough plasma levels of nicotine are in the range 5–15 ng/ml and levels at the time of smoking rise to 15–30 ng/ml.

The transcutaneous devices disclosed in U.S. Pat. No. 4,597,961 have substantial thickness viz 2 cm and hence are rather bulky. It is stated the onset of nicotine activity is in the range of 1–2 minutes with a duration of action of from 30–45 minutes. Hence, the device would have to be frequently applied, for example, hourly and even then it is doubtful whether adequate levels of nicotine would be achieved having regard to the specified dosage of 15 to 25 ng/l.

SUMMARY OF THE INVENTION

It is an object of the present invention to provide a method of administering nicotine in smoking cessation therapy, which on single daily application reproduces those plasma nicotine levels observed in habitual smokers in a manner which decreases or eradicates nicotine dependence in humans, thus concomitantly leading to an eradication of the harmful and undesirable health and social effects of smoking. It is also an object of the invention to provide a method and a preparation which will assist in breaking the smoking habit.

DETAILED DESCRIPTION OF THE INVENTION

According to the invention there is provided preparation for the once-daily percutaneous administration of nicotine which comprises nicotine uniformly distributed in a solid, semi-solid or mucilaginous medium which can be placed in intimate contact with the skin, said solid, semi-solid or mucilaginous medium being formed by adding a given amount of nicotine to a solution of a solidifying or gel-forming agent or mixture thereof in a suitable solvent or mixture of solvents and mixing or heating the mixture thereby obtained so as to form said solid, semi-solid or mucilaginous medium.

The term solidifying agent as used herein also embraces thickening, hardening, setting, suspending or like agents.

Suitable materials for use as the solidifying or gel-forming agent according to the invention include, for example, plant extracts, vegetable oils, gums, synthetic or natural polysaccharides, polypeptides, alginates, hydrocarbons, synthetic polymers, minerals and silicon compounds and mixtures thereof.

Suitable plant extracts include agar, ispaghula, psyllium, cydonia and ceratonia or a mixture thereof.

A suitable vegetable oil is hydrogenated castor oil.

Examples of suitable gums include guar gum, acacia gum, ghatti gum, karaya gum and tragacanth gum or a mixture thereof.

Suitable synthetic and natural polysaccharides include alkylcelluloses, hydroxyalkylcelluloses, cellulose ethers, cellulose esters, nitro celluloses, dextrin, agar, carrageenan, pectin, furcellaran and starch or starch derivatives and mixtures thereof. An example of a preferred starch derivative is sodium starch glycolate. Especially preferred polysaccharides include agar and carrageenan.

Suitable polypeptides include zein, gelatin, collagen and polygeline or a mixture thereof.

Suitable alginates include alginic acid, propylene glycol alginate and sodium alginate or a mixture thereof.

Preferred hydrocarbons include soft paraffin and hard paraffin, especially white petrolatum.

An especially preferred synthetic polymer is a carboxyvinyl polyme sold under the Trade Mark CARBOMER.

Suitable minerals include bentonite, hectorite, aluminium magnesium silicate and magnesium silicate or a mixture thereof.

Suitable compounds based on silicon include colloidal silicon dioxide, silicones, polysiloxanes and silica gels or a mixture thereof.

The term "agar" is used throughout the Specification and is synonymous with "agar-agar".

The solvent used is preferably water. However, the solvent used may also suitably be an alcohol such as ethanol or stearyl alcohol, glycerol, propylene glycol, polyethylene glycol or silicone or a mixture thereof, including a mixture with water.

The preparation when in the form of a solid or semi-solid preferably has a surface area in the range 2 to 15 $cm^2$, more especially 5 to 10 $cm^2$.

The thickness of the preparation is in the range 0.5 to 3 mm, more especially in the range 1 to 2 mm.

The preparation according to the invention preferably contains from 5 to 100 mg of nicotine or more especially 10 to 50 mg of nicotine.

The preparation according to the invention may also include an antimicrobial agent or a preservative. Suitable antimicrobial agents/preservatives include benzalkonium chloride, cetrimide (cetyltrimethylammonium bromide), benzoic acid, benzyl alcohol, Parabens (Trade Mark for the methyl-, ethyl-, propyl- and butyl-esters of para-hydroxybenzoic acid) chlorhexidine, chlorobutanol, phenylmercuric acetate, borate and nitrate, potassium sorbate, sodium benzoate, sorbic acid and thiomersal (mercurithiosalicylate) or a mixture thereof.

The preparation according to the invention may also include an antioxidant. Preferred antioxidants include sodium metabisulphite, butylated hydroxyanisole and butylated hydroxytoluene or a mixture thereof.

The preparation according to the invention may also include a pH-controlling agent. Preferred pH-controlling agents include citric acid and sodium citrate.

The preparation according to the invention may also include a plasticizer. Suitable plasticizers include diethylphthalate, dibutylphthalate and tributylcitrate or a mixture thereof.

The preparation according to the invention may also include a surfactant. Suitable surfactants include sodium lauryl sulphate, diethylene glycol monostearate, propylene glycol monostearate, polyethylene glycols as sold under the Trade Mark MACROGOL, polysorbates and polyvinyl alcohol or a mixture thereof.

The preparation according to the invention may also include a penetration enhancer. Suitable penetration enhancers include dimethylsulphoxide, N,N-dimethylacetamide, N,N-dimethylformamide, 2-pyrrolidone, N-methyl-2-pyrrolidone and 1-dodecyl azacycloheptan-2-one or a mixture thereof.

The preparation according to the invention may also include a humectant. A particularly preferred humectant is glycerol for use in a high humidity environment. As indicated above glycerol may also be used as a solvent in forming the preparation according to the invention and when used as such will confer humectant properties on the preparation.

Further the preparation according to the invention may also include a local anaesthetic. Suitable local anaesthetics include lidocaine, benzocaine, lignocaine, methocaine, butylaminobenzoate and procaine or a mixture thereof. The preparation would include a local anaesthetic mainly to suppress irritation at the site of application thereof.

Additionally, the preparation according to the invention may include a rubefacient. Particularly preferred rubifacients include camphor and menthol or a mixture thereof and other locally acting peripheral vasodilators.

The preparation according to the invention is preferably applied to the flexor surface of the forearm, including the wrist, and also the ankle. Such sites of application show the greatest consistency from individual to individual in terms of nicotine absorption relative to other sites for administration because of the amount of tissue at such sites. Blood vessels are found close to the surface of the skin at such sites which facilitates the uptake of nicotine into the systemic circulation.

On contact of the preparation according to the invention with the skin, the nicotine starts to migrate rapidly from the preparation to the humid interface at the point of contact and then through the skin and into the bloodstream. The rate and extent of this percutaneou absorption is dependent on several factors including:
 (a) The amount of nicotine in the preparation.
 (b) The surface area of the preparation.

As it is the skin itself that forms the rate controlling barrier and not the dosage form comprising the preparation, the effect of nicotine loading will only be observed in terms of systemic nicotine levels below a threshold loading level.

Below this threshold the amount of nicotine in the dosage form is the factor which determines the concentration gradient that in turn controls the rate of absorption. Above this threshold increasing drug loading has no effect on absorption as the ability of the skin to absorb nicotine is saturated. However, such drug loading does have the effect of prolonging the time course of drug delivery by providing a larger drug depot. In order to increase the extent of absorption above the threshold it is necessary to increase the area of absorption by increasing the surface area of the dosage form so that a larger area of the skin is in contact with the nicotine. The effect of changing the surface area for example at 4, 6, 8 and 12 $cm^2$ can be seen hereinafter in the Examples.

The preparation according to the invention can be presented in a number of devices and dosage forms for the percutaneous administration of nicotine. These devices and dosage forms may contain a nicotine impermeable layer so as to cause unidirectional administration of nicotine through the skin from the surface of the preparation in the device or dosage form exposed to the skin. Such devices and dosage forms include, but are not limited to, a device known under name PANODERM and which is the subject of our EP-A-0 117 027, a device known under the name DERMAFLEX and which is the subject of our EP-B-0 113 562, self adhesive patches, bandages and plasters, creams, gels, jellies, mucilages, ointments and pastes. The term mucilaginous medium as used herein embraces creams, gels, jellies, ointments and pastes.

The preparation according to the invention may be adapted for reception in a receptacle of a device which can be held in contact with the skin.

Means for securing transdermal patches to the body include, apart from adhesive means, straps, bracelets and like securing devices.

The present invention is also designed to provide, through percutaneous administration by way of the said devices and dosage forms, a highly cosmetically and aesthetically acceptable method of easily and discreetly administering nicotine in assisting the smoker to overcome the smoking habit.

With the present invention, it is possible to affix one of the said devices or dosage forms to the skin, so as to provide constant absorption of nicotine through the skin directly into the bloodstream, maintaining regular levels of nicotine in the blood. Therefore, the need to smoke a cigarette to obtain nicotine is eliminated, thereby eliminating ingestion of smoke and tar and thus breaking the smoking habit. The fact that this can be achieved with a device or dosage form which is administered only once every 24 hours provides for an additional aid to smoking cessation therapy in that it assists the smoker to overcome the psychological dependency associated with the habit of smoking on a frequent basis. Commercially available products such as nicotine containing gum need to be administered on a frequent basis, (practically every hour), throughout the course of any one day. This is a direct substitution for a similar smoking regimen and while, to a certain degree, the gum provides replacement plasma nicotine levels, it also serves to maintain the habit of frequent administration which can itself lead to a psychological dependence on the gum, thus rendering it even more difficult for the smoker to overcome the pharmacological and physiological dependence effects of nicotine. The present invention thus tackles both the physiological and psychological dependency parameters associated with smoking. By employing a succession of lower strengths of nicotine over several weeks or months, the nicotine level in the blood is gradually lowered, thus reducing nicotine dependency. As the skin is the rate controlling membrane in nicotine absorption, it is also possible in accordance with the invention, by varying the concentration of nicotine in said devices and dosage forms, and furthermore by varying the surface area of the nicotine containing portion of the said devices and dosage forms directly in contact with the skin, to adjust the extent of absorption of the nicotine and thereby mimic blood levels associated with virtually any level of smoking and achieve such levels over a 24 hour period with a single administration. This allows the smoker to effectively titrate the dosage in line with the extent of the smoking habit and/or urge.

In some individuals, it may be desirable to remove the device or dosage form which is affixed to the skin, in the evening before retiring to bed, and in these cases, appreciable morning trough levels of plasma nicotine in the range of 5 to 12 ng/ml are achieved. This ability to sustain residual plasma levels of nicotine for 8-10 hours after the device or dosage form has been removed from contact with the skin is another unique feature of the present invention.

In certain cases such as: when the smoker is applying the preparation according to the invention in the said device or dosage form for the first time or, when the individual is applying another dose after having detached the previous one some hours previously or, when an individual who has a particularly high nicotine requirement is replacing the existing dose, an initial 'burst' or priming dose of nicotine may be required to achieve rapid effective plasma levels to curb the nicotine craving or smoking urge. Such can be supplied by applying a device or dosage form in which an amount of nicotine is included in a layer of adhesive which is used to affix the said device or dosage form to the skin. Such a priming dose of nicotine may be included in a layer of adhesive material defining the skin contacting surface of the preparation and which layer is freely permeable to the nicotine contained in the solid, semi-solid or mucilaginous agar medium of said preparation. Alternatively, the priming dose of nicotine may be includediin a peripheral layer of adhesive defining part of the skin-contacting surface of a the preparation.

The invention also provides use of nicotine for the manufacture of a medicament for use in the once-daily, percutaneous administration of nicotine in a method for the treatment of withdrawal symptoms associated with smoking cessation and in which the nicotine is administered in an amount sufficient to maintain plasma levels of nicotine substantially equivalent to trough plasma levels resulting from intermittent smoking.

The invention also provides a method of treating withdrawal symptoms associated with smoking cessation, which method comprises administering once-daily, percutaneously to a person an amount of nicotine sufficient to maintain in said person plasma levels of nicotine substantially equivalent to trough plasma levels resulting from intermittent smoking.

Preferably, the amount of nicotine administered is sufficient to achieve a plasma nicotine concentration in excess of 2 ng/ml, more especially 5 ng/ml, within 1 hour after administration.

Also the amount of nicotine administered is preferably sufficient to achieve a plasma nicotine concentration in the range 2 to 100 ng/ml, more especially 5 to 30 ng/ml, over a period of from 1 to 24 hours.

Further, preferably, the amount of nicotine administered is progressively lowered over a period of time, such that the plasma level of nicotine is gradually lowered, thereby reducing nicotine dependency.

The invention also provides use of nicotine for the manufacture of a medicament for use in the once-daily, percutaneous administration of nicotine in a method for combating the psychological dependence that occurs through frequent smoking and in which the nicotine is administered in an amount sufficient to maintain plasma levels of nicotine substantially equivalent to trough plasma levels resulting from intermittent smoking.

The invention also provides a method for combating the psychological dependence that occurs through frequent smoking, which method comprises administering once-daily, percutaneously to a person an amount of nicotine sufficient to maintain in said person plasma levels of nicotine substantially equivalent to trough plasma levels resulting from intermittent smoking.

Preferably, the amount of nicotine administered is sufficient to achieve a plasma nicotine concentration in excess of 2 ng/ml, more especially 5 ng/ml, within 1 hour after administration.

Also the amount of nicotine administered is preferably sufficient to achieve a plasma nicotine concentration in the range 2 to 100 ng/ml, more especially 5 to 30 ng/ml, over a period of from 1 to 24 hours.

Further, preferably, the amount of nicotine administered is progressively lowered over a period of time, such that the plasma level of nicotine is gradually lowered, thereby reducing nicotine dependency.

In order to form the preparation according to the invention the thickening, hardening, setting, gelling, suspending or solidifying agent or a mixture of such agents is added to the solvent(s) at a concentration that will result in a suitably mucilaginous, semi-solid or solid mass. The mixture is mixed and/or heated, depending on the agent used, so as to produce a uniform medium. The nicotine is added to produce a concentration suitably in the range 0.5% to 25%, and preferably in the range 1% to 10%. Any other inactive ingredients and additional ingredients as hereinbefore specified are now added and the entire mixture is mixed to uniformity. This mixture is now used to form the final dosage form which may be any of the following:

(a) a solid or semi-solid disc or patch formed by moulding, cutting, punching or slicing of the mixture.

(b) a cream.

(c) a mucilage.

(d) a gel.

(e) a paste.

(f) a jelly.

(g) an ointment.

The dosage form may now be incorporated into any suitable device for attachment to the skin as indicated above.

The invention will be further illustrated by the following Examples.

EXAMPLE 1

To 20 g of water was added 0.5 g of carrageenan. This mixture was heated to boiling and then allowed to cool gradually. While still in its liquid state 1.04 g of nicotine was added and the mixture was agitated to ensure uniformity. The liquid mixture was then poured onto several 20 cm×20 cm glass plates equipped with TEFLON (TEFLON is a Trade Mark) dividers approximately 0.75 mm in height. A second similar glass plate was placed over the liquid supported by the TEFLON dividers. The liquid was allowed to cool to room temperature and solidified into a sheet of uniform thickness (approximately 0.75 mm). The sheet was then cut into square patches 2 cm×2 cm, each weighing approximately 0.3 g with a surface area of 4 $cm^2$ and each containing 15 mg of nicotine. The patches were wrapped in aluminium foil to prevent dehydration.

In-vivo studies established that plasma nicotine levels over a 24 hour period following the application of a single patch prepared according to the above Example ranged from about 7 ng/ml to about 15 ng/ml.

EXAMPLE 2

Patches were prepared as per Example 1, except that 0.693 g of nicotine was added to the water/carrageenan mixture and the sheet was cut into circular discs (0.75 mm thick) of diameter 3.2 cm, each weighing approximately 0.6 g, with a surface area of 8 cm² and each containing 20 mg of nicotine.

The plasma nicotine levels for the above-prepared disc ranged from about 12 ng/ml to about 24 ng/ml over a 24 hour period.

EXAMPLE 3

To 50 g of Silicone Gel (Dow Corning Q7-2218) Part A was added 25 g of a 20% solution of nicotine in water, 5 g camphor, 2.5 g of dimethylsulphoxide and 2.5 g of glycerol. The ingredients were mixed to uniformity. 65 g of Silicone Gel (Dow Corning Q7-2218) Part B was then added and the mixture was further agitated to ensure uniformity. The mixture was cured overnight to ensure proper gel formation. 0.6 g portions of the gel, equivalent to 20 mg of nicotine, were weighed into a performed circular device, sold under the Trade Mark PANODERM of internal diameter 3.2 cm giving a surface area of 8 cm².

The plasma nicotine levels for the above Example ranged from about 12 ng/ml to about 22 ng/ml over a 24 hour period.

EXAMPLE 4

To 100 g of water was added 10 g of powdered gelatin and 10 g of dextrin. The mixture was heated to boiling. While mixing, the following were also added, 0.01 g of benzalkonium chloride, 0.1 g of sodium metabisulphite, 4.8 g of nicotine. The hot liquid was poured onto glass plates as described in Example 1. After setting the gel was cut into discs 0.95 mm thick and 3.2 cm in diameter, each weighing 0.65 g with a surface area of 8 cm² and each containing 25 mg of nicotine.

The above-prepared discs yielded plasma nicotine levels ranging from about 15 ng/ml to about 25 ng/ml over 24 hours.

EXAMPLE 5

A product was made as per Example 1 with 0.05 g of methylparaben added to the hot water/carrageenan mixture.

EXAMPLE 6

50 g of stearyl alcohol and 50 g of white petrolatum were melted by heating to 75° C. 0.05 g of methylparaben, 0.3 g of propylparaben, 2 g of sodium lauryl sulphate, 24 g of propylene glycol and 8 g of nicotine were dissolved in 84 g of water. The aqueous solution was heated to 75° C. and added to the melted stearyl alcohol/ petrolatum mixture. The entire mixture was allowed to cool with constant stirring and congealed into a uniform cream. 0.5 g portions of the cream, equivalent to 20 mg of nicotine, were weighed into circular transdermal delivery devices sold under the Trade Mark PANODERM of internal diameter 2.75 cm giving a surface area of 6 cm².

The plasma nicotine levels for this cream ranged from about 21 ng/ml to about 33 ng/ml over 24 hours.

EXAMPLE 7

A product was made as per Example 1 except that 1.4 g of nicotine was added to the water/carrageenan mixture and the patch was cut into rectangular patches measuring 3×4 cm, each weighing 0.9 g with a surface area of 12 cm².

The plasma nicotine levels for this patch ranged from about 8 ng/ml to about 16 ng/ml over 24 hours.

EXAMPLE 8

To 20 g of water was added 0.8 g of agar. This mixture was heated and allowed to cool gradually, while still in its liquid state 0.6664 ml of nicotine was added and the mixture was agitated to ensure uniformity. The liquid mixture was then poured onto several 20 cm×20 cm glass plates equipped with TEFLON (TEFLON is a Trade Mark) dividers approximately 1.31 mm in height. A second similar glass plate was placed over the liquid supported by the TEFLON dividers. The liquid was allowed to cool to room temperature and solidified into a sheet of uniform thickness (approximately 1.31 mm in thickness). The sheet was then cut into discs, each weighing approximately 0.76 g with a surface area of 5.3 cm² and each containing 25 mg of nicotine. The patches were wrapped in aluminium foil to prevent dehydration.

Over a 24 hour period, the above-prepared disc produced plasma nicotine levels ranging from about 8 ng/ml to about 2 ng/ml.

EXAMPLE 9

To 20 g of water was added 0.8 g of agar. This mixture was heated and allowed to cool gradually, while still in its liquid state 0.6664 ml of nicotine was added and the liquid agitated to ensure uniformity. The mixture, while still in the liquid state, was then poured into a formed coated aluminium die resulting in a disc of gel of 1.31 mm in thickness and surface area of 5.3 cm² following solidification and edged around the circumference by 1 cm of aluminium foil. The disc so prepared was then sealed by a coated foil circular seal edged by 1 cm of adhesive. On removal of the seal the disc selectively adhered to the adhesive side of the device, and the aluminium die in which the disc was formed was discarded. The device so prepared provides excellent skin contact in use.

EXAMPLE 10

To a 20 g 15:5 (w/w) mixture of water and glycerol was added 0.8 g of agar. This mixture was heated and allowed to cool gradually. While still in its liquid form 0.6664 ml of nicotine was added and the liquid agitated to ensure uniformity. The mixture while still in the liquid state, was poured into a formed coated aluminium die resulting in a disc of gel of 1.31 mm in thickness and surface area of 5.3 cm² upon solidification and edged around the circumference by 1 cm of aluminium foil. The disc so prepared was then sealed by a coated foil circular seal edged by 1 cm of adhesive. On removal of the seal the disc selectively adhered to the adhesive side of the device and the aluminium die in which the disc was formed was discarded. The device so prepared provides excellent skin contact in use and produces plasma nicotine levels ranging from about 11 ng/ml to about 34 ng/ml over 24 hours.

EXAMPLE 11

To a 20 g 90:10 (w/w) water: ethanol mixture was added 0.8 g agar. This mixture was heated and allowed to cool gradually, while still in its liquid form 0.6664 ml of nicotine was added and the mixture agitated to ensure uniformity. The mixture while still in the liquid state was poured into a formed coated aluminium die resulting in a disc of gel of 1.31 mm in thickness and surface area of 5.3 cm² upon solidification and edged around the circumference by 1 cm of aluminium foil.

The disc so prepared was then sealed by a coated foil circular seal edged by 1 cm of adhesive. On removal of the seal the disc selectively adhered to the adhesive side of the device and the aluminium die in which the disc was formed was discarded. The device so prepared provides excellent skin contact in use.

EXAMPLE 12

A device was prepared as in Example 9 with 0.05 g of methylparaben added to the hot water: agar mixture.

EXAMPLE 13

A device was prepared as in Example 10 with a 15:5 (w/w) mixture of water: PEG (polyethylene glycol) 400 in place of water and glycerol.

EXAMPLE 14

A device was prepared as in Example 9 having a nicotine concentration of 25 mg/g with a surface area of 7.64 cm$^2$ and thickness of 1.31 mm.

EXAMPLE 15

500 g of water was heated to boiling. 25 g of carrageenan was added and the mixture was boiled for approximately 5–10 minutes. The solution was allowed to cool to between 50° C. and 60° C. 33 g of nicotine was added and allowed to dissolve. The solution was diluted to 1,000 g with water. The mixture while still in its liquid state was poured (0.9091 g) into a formed coated aluminium die. The resulting solidified disc had a thickness of 1.30 mm, a surface area of 7.0 cm$^2$ and contained 30 mg of nicotine. The formed disc was sealed by a circle of aluminium coated with an impervious membrane and a coat of gelatin. On removal of the seal, the disc selectively adhered to the gelatin side of the aluminium seal. Adhesive tape was used to secure the disc to the skin. The disc so prepared produces plasma nicotine levels ranging from about 3 ng/ml to about 16 ng/ml over a 24 hour period.

In-Vivo Studies

All of the foregoing in-vivo studies were performed in healthy habitually smoking volunteers who had abstained from smoking for 36 hours before the study and for the duration of the study itself. The study site was a non-smoking environment which was nicotine free. The subjects were not permitted to consume tea, coffee or Cola during the study. The average number of volunteers for the various studies was six. Pre-study physical examinations and electrocardiogram (ECG) were normal and pre and post study haematology, blood biochemistry and urinalysis were also normal in all subjects. Blood samples (10 ml) were obtained at 0 hours immediately before the dosage form was applied onto the skin and at specific times thereafter. Plasma was obtained by centrifugation of the blood samples at 2° C. and plasma nicotine levels were measured by a capillary gas chromatography method. The Examples tested above demonstrate plasma nicotine levels which simulate those obtained with usual smoking.

The discs prepared according to Example 15 were evaluated in a quit-rate study. When compared to subjects receiving placebo patches, the application of the nicotine-containing patches resulted in a positive reduction in cigarette smoking.

It is a unique feature of the present invention that the development and evaluation of the in-vivo performance of the system or systems is based solely on studies in human volunteers. This contrasts with the use of animal models commonly employed by other investigators in the area of transdermal drug delivery, particularly in the light of the marked differences in dermal and transdermal absorption and pharmacokinetic characteristics between human and animal models.

What is claimed is:

1. A preparation for the once-daily, percutaneous administration of nicotine which comprises nicotine uniformly distributed in a solid or semi-solid medium which can be placed in intimate contact with the skin, said solid or semi-solid medium comprising a given amount of nicotine in a solution of a solidifying or gel-forming agent or mixture thereof in a suitable solvent or mixture of solvents, said mixture thereby obtained having been mixed or heated to form said solid or semi-solid medium, wherein said medium is effective to permit controlled release of said nicotine to the skin.

2. A preparation according to claim 1, wherein the solvent used is selected from the group consisting of water, ethanol, stearyl alcohol, glycerol, ethylene glycol, propylene glycol, and silicone or a mixture thereof.

3. A preparation according to claim 1, which is in the form of a solid or semi-solid and has a surface area in the range 2 to 15 cm$^2$.

4. A preparation according to claim 3, which has a thickness in the range 0.5 to 3 mm.

5. A preparation according to claim 1, which is in the form of a cream, gel, jelly, mucilage, ointment or paste.

6. A preparation according to claim 1, wherein the solidifying or gel-forming agent is selected from the group consisting of plant extracts, vegetable oils, gums, synthetic or natural polysaccharides, polypeptides, alginates, hydrocarbons, synthetic polymers, minerals and silicon compounds or a mixture thereof.

7. A preparation according to claim 6, wherein the solidifying or gel-forming agent is a plant extract selected from the group consisting of agar, ispaghula, psyllium, cydonia and ceratonia or a mixture thereof.

8. A preparation according to claim 6, wherein the solidifying or gel-forming agent is hydrogenated castor oil.

9. A preparation according to claim 6, wherein the solidifying or gel-forming agent is a gum selected from the group consisting of guar gum, acacia gum, ghatti gum, karaya gum and tragacanth gum or a mixture thereof.

10. A preparation according to claim 6, wherein the solidifying or gel-forming agent is a synthetic or natural polysaccharide selected from the group consisting of alkylcelluloses, hydroxyalkylcelluloses, cellulose ethers, cellulose esters, nitro celluloses, dextrin, agar, carrageenan, pectin, furcellaran and starch or starch derivatives and mixtures thereof 11. A preparation according to claim 6, wherein the solidifying or gel-forming agent is a polypeptide selected from the group consisting of zein, gelatin, collagen and polygeline or a mixture thereof.

12. A preparation according to claim 6, wherein the solidifying or gel-forming agent is an alginate selected from the group consisting of alginic acid, propylene glycol alginate and sodium alginate or a mixture thereof.

13. A preparation according to claim 6, wherein the solidifying or gel-forming agent is a hydrocarbon selected from the group consisting of soft paraffin and hard paraffin or a mixture thereof.

14. A preparation according to claim 6, wherein the solidifying or gel-forming agent is carboxyvinyl polymer.

15. A preparation according to claim 6, wherein the solidifying or gel-forming agent is a mineral selected from the group consisting of bentonite, hectorite, aluminium magnesium silicate and magnesium silicate or a mixture thereof.

16. A preparation according to claim 6, wherein the solidifying or gel-forming agent is a silicon compound selected from the group consisting of colloidal silicon dioxide, silicones, polysiloxanes and silica gels or a mixture thereof.

17. A preparation according to claim 1, which contains from 5 to 100 mg of nicotine.

18. A preparation according to claim 17, which contains from 10 to 50 mg of nicotine.

19. A preparation according to claim 1, which contains one or more additional components selected from the group consisting of an antimicrobial agent or a preservative, an antioxidant, a pH-controlling agent, a plasticizer, a surfactant, a penetration enhancer, a humectant, a local anaesthetic and a rubefacient or a mixture thereof.

20. A preparation according to claim 19, which contains an anti-microbial agent or a preservative selected from the group consisting of benzalkonium chloride, cetyltrimethylammonium bromide, benzoic acid, benzyl alcohol, the methyl-, ethyl-, propyl- and butyl-esters of para-hydroxybenzoic acid or a mixture thereof, chlorhexidine, chlorobutanol, phenylmercuric acetate, borate or nitrate, potassium sorbate, sodium benzoate, sorbic acid and mercurithiosalicylate or a mixture thereof.

21. A preparation according to claim 19, which contains an antioxidant selected from the group consisting of sodium metabisulphite, butylated hydroxyanisole and butylated hydroxytoluene or a mixture thereof.

22. A preparation according to claim 19, which contains a pH-controlling agent selected from the group consisting of citric acid and sodium citrate.

23. A preparation according to claim 19, which contains a plasticizer selected from the group consisting of diethylphthalate and tributylcitrate or a mixture thereof.

24. A preparation according to claim 19, which contains a surfactant selected from the group consisting of sodium lauryl sulphate, diethylene glycol monostearate, propylene glycol monostearate, polyethylene glycols, polysorbates and polyvinyl alcohol or a mixture thereof.

25. A preparation according to claim 19, which contains a penetration enhancer selected from the group consisting of dimethylsulphoxide, N,N-dimethylacetamide, N,N-dimethylformamide, 2-pyrrolidone, N-methyl-2-perrolidone and 1-dodecyl azacyclo-heptan-2-one or a mixture thereof.

26. A preparation according to claim 19, which contains glycerol as a humectant.

27. A preparation according to claim 19, which contains a local anaesthetic selected from the group consisting of lidocaine, benzocaine, lignocaine, methocaine, butylaminobenzoate and procaine or a mixture thereof.

28. A preparation according to claim 19, which contains a rubefacient selected from the group consisting of camphor and menthol, or a mixture thereof.

29. A preparation according to claim 1, which is adapted to be received in a receptacle of a device which can be held in contact with the skin.

30. A preparation according to claim 1, which is incorporated in self-adhesive patch bandage or a plaster.

31. A preparation according to claim 1, which includes a priming dose of nicotine in a layer of adhesive material defining the skin-contacting surface of the preparation and which layer is freely permeable to the nicotine contained in said medium.

32. A preparation according to claim 1, which includes a priming dose of nicotine in a peripheral layer of adhesive material defining part of the skin-contacting surface of the preparation.

33. A method of treating withdrawal symptoms associated with smoking cessation, which method comprises administering once-daily, percutaneously to a person in need of said treatment an amount of nicotine sufficient to maintain in said person plasma levels of nicotine substantially equivalent to trough plasma levels resulting from intermittent smoking, wherein said nicotine is distributed in a solid, semi-solid or muciloginous medium which is effective to permit controlled release of said nicotine to the skin.

34. A method according to claim 33, wherein the amount of nicotine administered is sufficient to achieve a plasma nicotine concentration in excess of 2 ng/ml within 1 hour after administration.

35. A method according to claim 33, wherein the amount of nicotine administered is sufficient to achieve a plasma nicotine concentration in excess of 5 ng/ml within 1 hour after administration.

36. A method according to claim 33, wherein the amount of nicotine administered is sufficient to achieve a plasma nicotine concentration in the range 2 to 100 ng/ml over a period from 1 to 24 hours.

37. A method according to claim 33, wherein the amount of nicotine administered is sufficient to achieve a plasma nicotine concentration in the range 5 to 30 ng/ml over a period of from 1 to 24 hours.

38. A method according to claim 33, wherein the amount of nicotine administered is progressively lowered over a period of time, such that the plasma level of nicotine is gradually lowered, thereby reducing nicotine dependency.

39. A method for combating the psychological dependence that occurs through frequent smoking, which method comprises administering once-daily, percutaneously to a person in need of said treatment an amount of nicotine sufficient to maintain in said person plasma levels of nicotine substantially equivalent to trough plasma levels resulting from intermittent smoking, wherein said nicotine is distributed in a solid, semi-solid or mucilaginous medium which is effective to permit controlled release of said nicotine to the skin.

40. A method according to claim 39, wherein the amount of nicotine administered is sufficient to achieve a plasma nicotine concentration in excess of 2 ng/ml within 1 hour after administration.

41. A method according to claim 39, wherein the amount of nicotine administered is sufficient to achieve a plasma nicotine concentration in excess of 5 ng/ml within 1 hour after administration.

42. A method according to claim 39, wherein the amount of nicotine administered is sufficient to achieve a plasma nicotine concentration in the range 2 to 100 ng/ml over a period of from 1 to 24 hours.

43. A method according to claim 39, wherein the amount of nicotine administered is sufficient to achieve a plasma nicotine concentration in the range 5 to 30 ng/ml over a period of from 1 to 24 hours.

* * * * *